United States Patent
Foster

(12) 
(10) Patent No.: US 8,339,588 B2
(45) Date of Patent: Dec. 25, 2012

(54) PORTABLE EGG CANDLING AND CONTAINMENT TRANSFER APPARATUS AND METHOD

(76) Inventor: Lance Foster, Collinsville, AL (US)

( * ) Notice: Subject to any disclaimer, the term of this patent is extended or adjusted under 35 U.S.C. 154(b) by 466 days.

(21) Appl. No.: 12/694,682

(22) Filed: Jan. 27, 2010

(65) Prior Publication Data

US 2010/0188650 A1 Jul. 29, 2010

Related U.S. Application Data

(60) Provisional application No. 61/147,744, filed on Jan. 27, 2009.

(51) Int. Cl.
*A01K 43/00* (2006.01)
*G01N 33/08* (2006.01)

(52) U.S. Cl. .......................................... 356/61; 356/56

(58) Field of Classification Search .............. 356/52–68, 356/239.4
See application file for complete search history.

(56) References Cited

U.S. PATENT DOCUMENTS

| | | | | |
|---|---|---|---|---|
| 808,177 | A | * | 12/1905 | Shoemaker ...................... 72/347 |
| 1,475,248 | A | * | 11/1923 | Shafer ............................ 118/425 |
| 1,519,896 | A | * | 12/1924 | Armistead et al. .............. 356/55 |
| 1,741,929 | A | * | 12/1929 | Gillespie ......................... 356/56 |
| 2,144,657 | A | * | 1/1939 | Harbison ......................... 356/65 |
| 2,403,705 | A | * | 7/1946 | Bramson ......................... 356/59 |
| 4,830,564 | A | * | 5/1989 | Walker et al. .................. 414/405 |
| 5,898,488 | A | | 4/1999 | Kuhl |
| 6,750,954 | B2 | | 6/2004 | Hebrank et al. |

OTHER PUBLICATIONS

Mississippi State University Extension Service; "Care and Incubation of Hatching Eggs"; 5 pages; www.msstate.edu/dept/poultry/hatch.htm; printed Jan. 26, 2009.

Natureform Hatcheries, Jacksonville, Florida; Instruction Book No. 9; "Eggmatic Transfer"; 2 pages; date unknown.

* cited by examiner

*Primary Examiner* — Tarifur Chowdhury
*Assistant Examiner* — Michael P Lapage
(74) *Attorney, Agent, or Firm* — Gardner Groff Greenwald & Villanueva, PC

(57) ABSTRACT

A portable egg candling and containment transfer apparatus including a movable base, a frame extending up from the base, a movable elevator deck movable between an elevated position and a lowered position, and a mechanism for raising and lowering the elevator deck. The apparatus further includes an inverting candling table pivotally mounted to the frame and having a pan with sidewalls and a floor. The pan is adapted for receiving and supporting incubator trays thereon. The pan houses at least one electric light fixture with at least one lamp for producing light for candling eggs positioned over the inverting candling table. The apparatus further includes at least one clamp for securing a hatchery basket over the pan and at least one latch for securing the inverting candling table in faceup/facedown positions.

11 Claims, 17 Drawing Sheets

PORTABLE EGG CANDLING AND CONTAINMENT TRANSFER APPARATUS AND METHOD

CROSS-REFERENCE TO RELATED APPLICATION

This application claims the priority benefit of U.S. Provisional Patent Application Ser. No. 61/147,744, filed Jan. 27, 2009, which is hereby incorporated herein by reference.

FIELD OF THE INVENTION

The present invention relates generally to an apparatus and method for candling bird eggs during incubation and for transferring such eggs from incubation trays to hatchery baskets.

BACKGROUND OF THE INVENTION

In many poultry farming and harvesting applications, the production of eggs and poultry meat is done on such a vast scale that significant automatic equipment and processes are employed. Indeed, such farming and harvesting can seem industrial in scope and manner.

However, there are many instances in which birds or bird eggs are produced in much smaller numbers. For example, quail and quail eggs are produced in numbers much, much smaller than chickens and chicken eggs. As such, the highly automated machinery and processes often employed in the production of chickens and chicken eggs are impractical for the production of quail and quail eggs. Such is also true for pheasants and other specialty birds, including specialty chickens like bantam hens.

SUMMARY OF THE INVENTION

In a first preferred form, the present invention comprises a portable egg candling and containment transfer apparatus to allow a user to manually, albeit with some assistance from the apparatus, candle batches of eggs once they are removed from an incubator and then to transfer the eggs from incubation trays to a hatching basket. A portable egg candling and containment transfer apparatus according to the first preferred form of the invention preferably includes a movable base and a frame extending up from the base. Preferably, the apparatus includes a movable elevator deck which is movable between an elevated position and a lowered position. and a mechanism for raising and lowering the elevator deck. The apparatus preferably also includes an inverting candling table pivotally mounted to the frame and having a pan with sidewalls and a floor, the pan being adapted for supporting incubator trays positioned thereover. Preferably, the pan houses at least one electric light fixture with at least one lamp for producing light for candling eggs positioned over the inverting candling table. Preferably, at least one clamp is provided for securing a hatchery basket over the pan. Also preferably, at least one latch is provided for securing the inverting candling table in faceup/facedown positions.

Such an apparatus can be of great assistance to a user who needs to candle incubating eggs and then in transferring the incubating eggs from incubator trays to hatching or hatchery baskets to complete the incubation and hatching.

Optionally, the portable egg candling and containment transfer apparatus according to a first preferred form of the invention includes a hand-operated mechanism for raising and lowering the movable elevator deck. Also optionally, a catch is provided for securing the elevator deck in the raised position.

In the first preferred form of the invention, it is preferred, although not required, that the pan includes a peripheral ledge for supporting incubator trays and an upstanding lip for positioning the incubator trays over the peripheral ledge. Optionally, cutouts can be formed in the peripheral ledge to provide hand access for grasping edges of the trays.

Optionally, the apparatus includes a hand-operated electric switch for controlling the at least one lamp. In one manner of carrying out the invention, the at least one lamp can comprise multiple fluorescent lamps.

Optionally, the at least one clamp comprises a pair of hand-operated clamps and the mechanism for raising and lowering the movable deck comprises an overhead handle which can be grasped and pulled downwardly to raise the movable deck.

To use the apparatus, typically one would push the apparatus over near an incubator and open the door of the incubator. One would then withdraw a couple of trays of eggs from the incubator and load them onto the inverting candling table. After loading the trays onto the candling table, one turns on the candling lamps and performs a visual inspection of the eggs. Any non-fertile or defective eggs are removed and the lamps are then turned off. A hatchery basket is then placed over the trays and clamped to the top of the candling table. The candling table is then unlatched and the user rotates (inverts) the candling table, the trays, the eggs, and the hatchery basket all together.

With the table now inverted, and the hatchery basket supported by the clamps, the user pulls downwardly on the overhead handle to raise the elevator deck to support the hatchery basket from beneath. The user then latches the handle mechanism to secure it in place and unclamps the hatchery basket from the candling table. With the hatchery basket now unclamped, the user next unlatches the handle mechanism and lowers the elevator deck to lower the hatchery basket away from the candling table. The user then removes the hatchery basket from the apparatus and stacks it. With the hatchery basket containing eggs now stacked, the user removes the now freed and upside-down incubator trays. To make the apparatus ready for the next cycle, the user re-inverts the candling table and latches it in place, making it ready to receive another pair of incubator trays.

DETAILED DESCRIPTION

Figure 1:
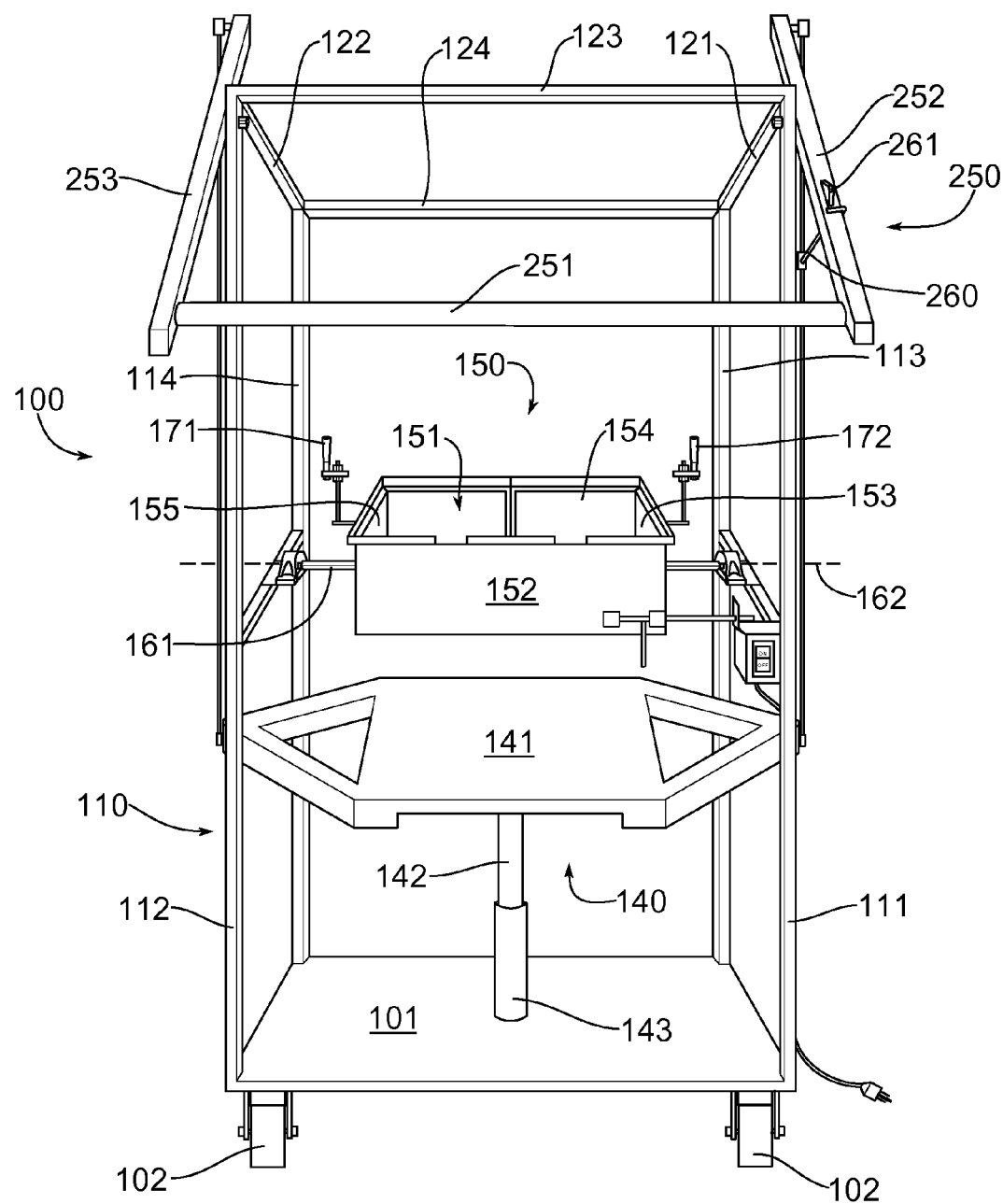
FIG. 1 is a front perspective illustration of a portable egg candling and containment transfer apparatus according to a first preferred form of the invention.

Referring now to the drawing figures, wherein like reference numerals represent like parts throughout the several views, FIGS. 1-20 depict a portable egg candling and containment transfer apparatus 100 and its use according to a first preferred form of the invention. As shown in these figures, the apparatus 100 includes a movable base 101 supported upon the ground by a plurality of casters 102. At least two of the casters 102 are lockable casters so that the movable base can be securely positioned in one spot. The movable base 101 as depicted comprises a sheet-metal platform. Those skilled in the art will recognize that other forms can be employed. For example, movable base 101 could be an open space frame, perforated metal, etc. The movable base 101 can include a peripheral frame supporting a sheet-metal cover, in which the casters 102 can be rigidly secured to the peripheral frame.

Figure 2:
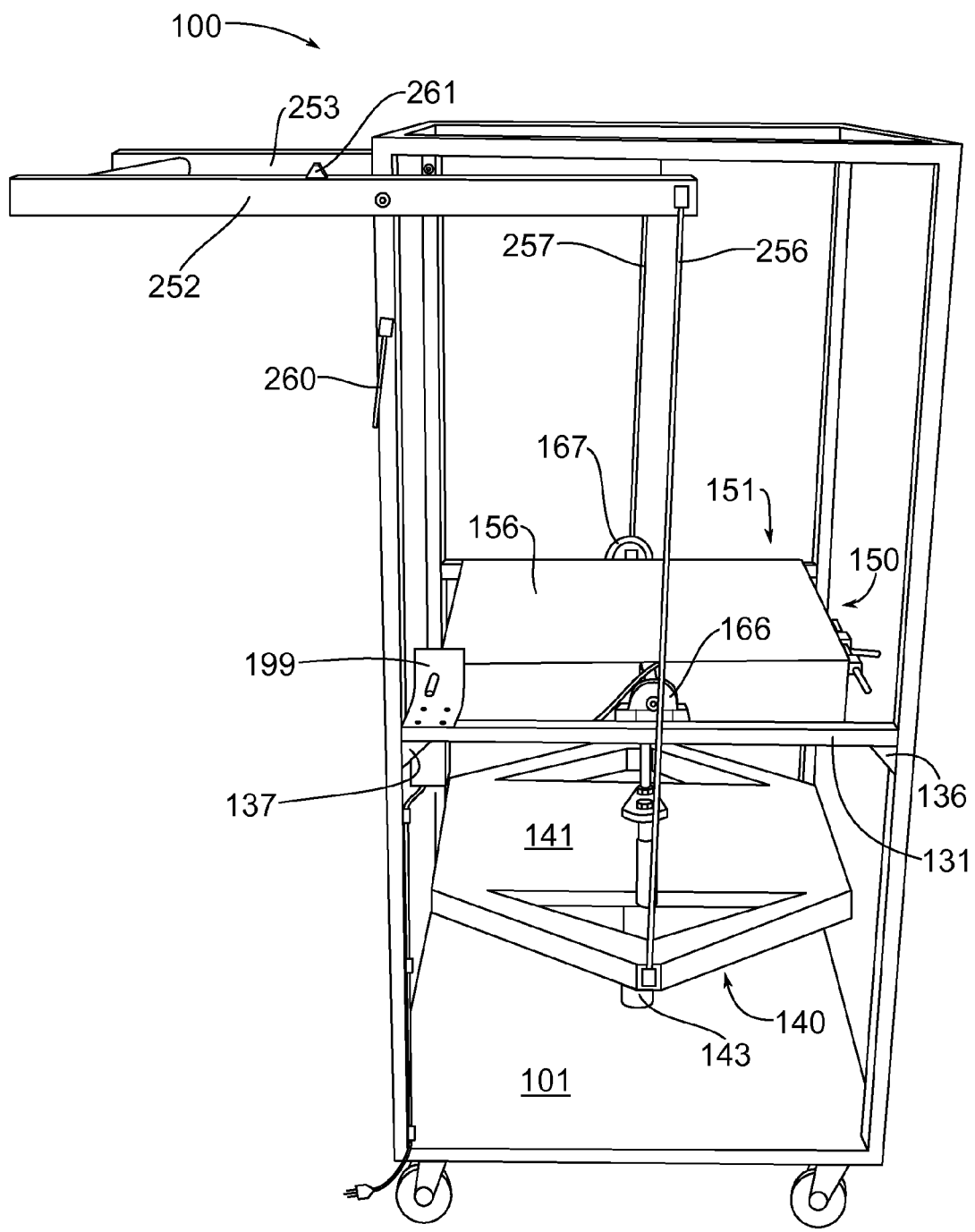
FIG. 2 is a right side perspective illustration of the portable egg candling and containment transfer apparatus of FIG. 1.

Extending out from the movable base 101 is a framework 110. The framework includes upright stanchions 111, 112, 113, and 114. The stanchions extend perpendicularly to the movable base 101 and are connected at the top thereof by a canopy framework 120, including cross members 121, 122, 123, and 124. Positioned part way up the sides of the framework 110 are additional cross members or side rails 131 and 132. For additional support and bracing, side rails 131, 132 are reinforced with gussets, such as gussets 136, 137, as seen in FIG. 2.

Those skilled in the art will recognize that while the framework 110 is shown as a space frame, a similar result can be achieved by cabinet-type construction using sheet-metal to form an enclosure, with the enclosure providing the structural rigidity otherwise provided by this space frame shown herein.

A movable elevator 140 is movably supported upon the movable base 101. The movable elevator 140 includes an elevator platform or deck 141, a tubular guided post 142, and a guiding sleeve 143. Guided post 142 is slidingly received within the guiding sleeve 143 to provide smooth, guided movement up and down for the elevator platform or deck 141. As shown herein, the platform or deck 141 is generally rectangular with a pair of extending, angled arms welded to each other at the end of the rectangle to form generally pointed ends on opposite sides of the deck 141. While the deck 141 is shown as having rectangular openings formed therein, those skilled in the art recognize that such openings can be dispensed with. Moreover, the overall shape of the deck 141 can be varied, as desired.

The inverting candling table 150 is generally positioned above the movable elevator 140. The inverting candling table 150 includes a pan 151 having sides 152, 153, 154, and 155, and further having a bottom 156. The pan 151 is pivotally mounted to the side rails upon a pivot axle 161 for pivotal rotation about a pivot axis 162. As shown, the pivot axis 162 is not centered in the pan 151, but instead is positioned near the bottom of the pan such that when the inverting candling table 150 is inverted, the clearance beneath the underside of the pan varies between a minimum amount and a maximum amount. The ends of the pivot axle 161 are received in pillow block bearings 166, 167, which are in turn mounted to the side rails 131 and 132.

Figure 4:
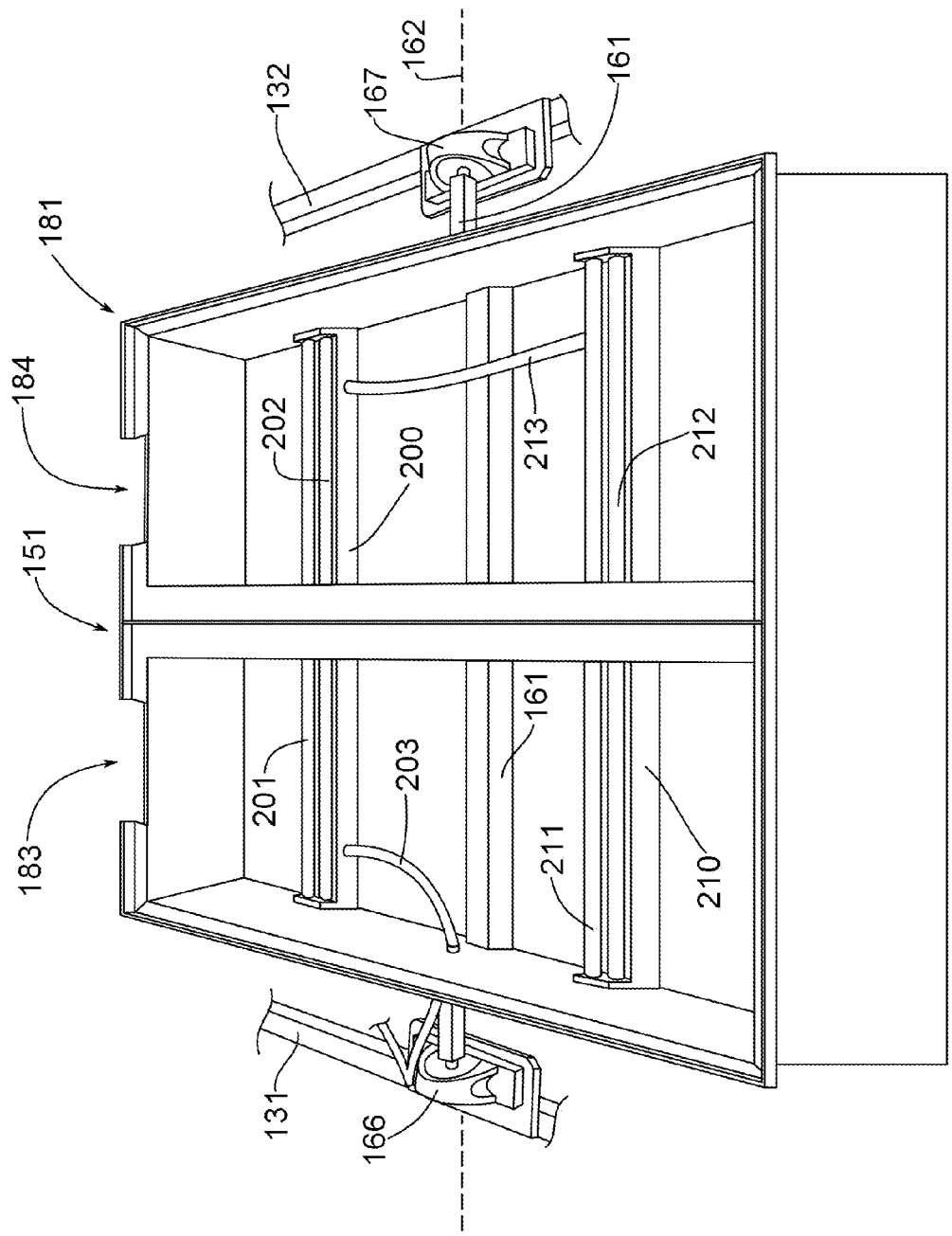
FIG. 4 is a perspective illustration of an inverting candling table portion of the portable egg candling and containment transfer apparatus of FIG. 1.

Two hand-operated clamps 171 and 172 are positioned on opposite ends of the pan 151 for securing a hatchery basket atop a peripheral ledge portion of the pan 151. As best seen in FIG. 4, the pan 151 includes a peripheral ledge 181 which extends horizontally and peripherally around the upper edge of the pan 151. The ledge 181 also includes an upstanding (vertical) railing to help position and hold incubator trays in place atop the pan 151. The ledge 181 also includes a pair of cut outs or openings 183, 184 to provide access for gripping the incubator trays once they are dropped into place on top of the pan 151. This facilitates the removal of incubator trays from the pan 151.

Figure 3:
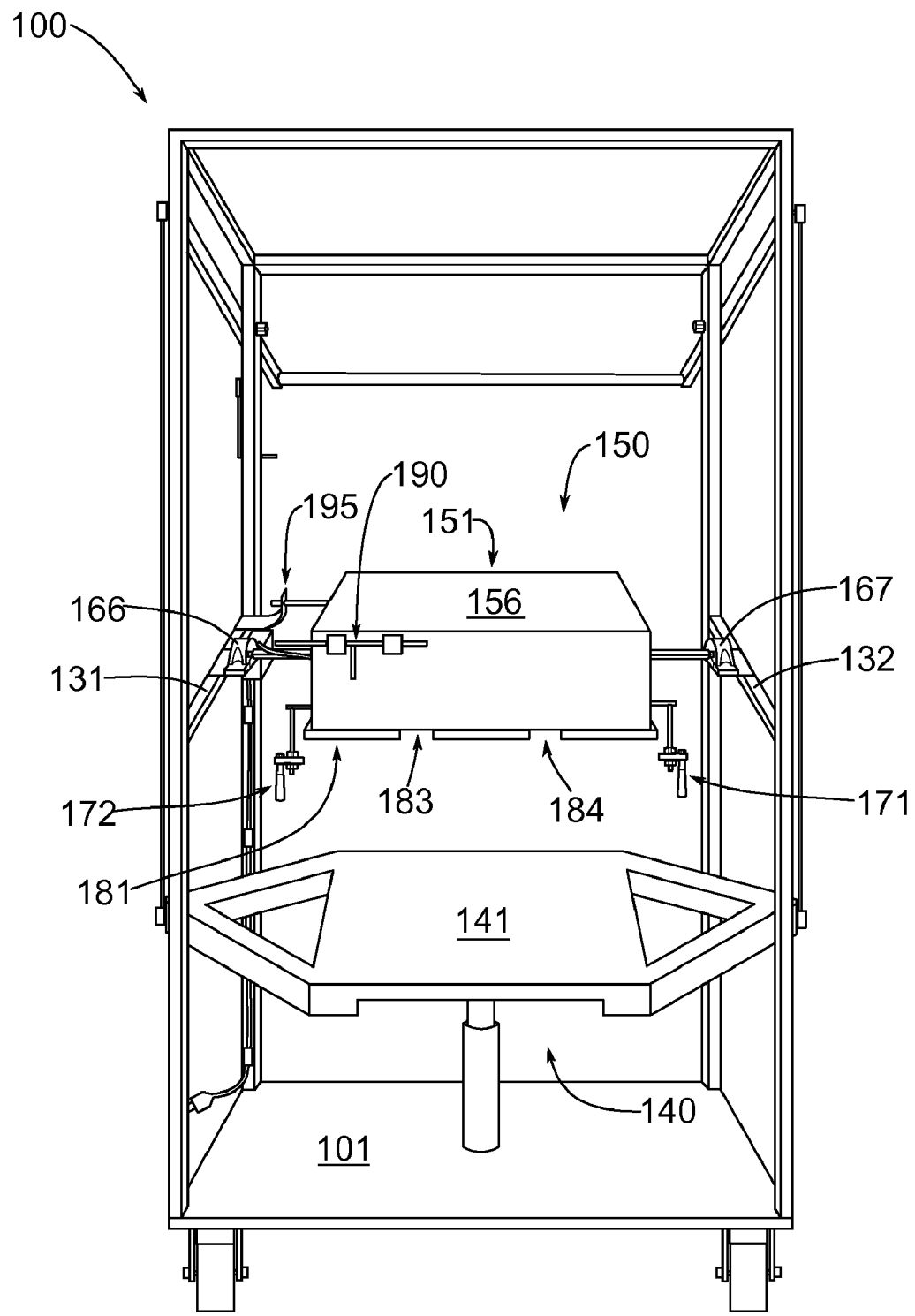
FIG. 3 is a rear perspective illustration of the portable egg candling and containment transfer apparatus of FIG. 1.

Two sliding bolt-style latches 190, 195 are secured to the pan 151 for cooperation with a latch striker plate 199. The latch striker plate 199 is rigidly secured to the framework. The latches 190, 195 each include a movable bolt, such as bolt 191, for movement between a retracted position withdrawn from the striker plate 199 and an extended position in which the bolt extends through the striker plate 199 for securing the pan in place. The latches are configured and positioned to allow the pan 151 to be secured in a face-up position as shown in FIG. 1 and secured in a face-down position as shown in FIGS. 2 and 3.

Referring now to FIG. 4, the interior of the pan 151 is considered in greater detail. As shown herein, two fluorescent light fixtures 200, 210 are secured to the floor or bottom 156. Each light fixture 200, 210 includes a pair of elongated fluorescent tube lamps, such as lamps 201, 202 and 211, 212. As depicted, the lamps can be 24 inch lamps, although those skilled in the art will appreciate that other types of illumination can be used as desired. Electric power is delivered to the first light fixture 200 by cord 203 and then is delivered on to the second light fixture by cord 213.

Figure 5:
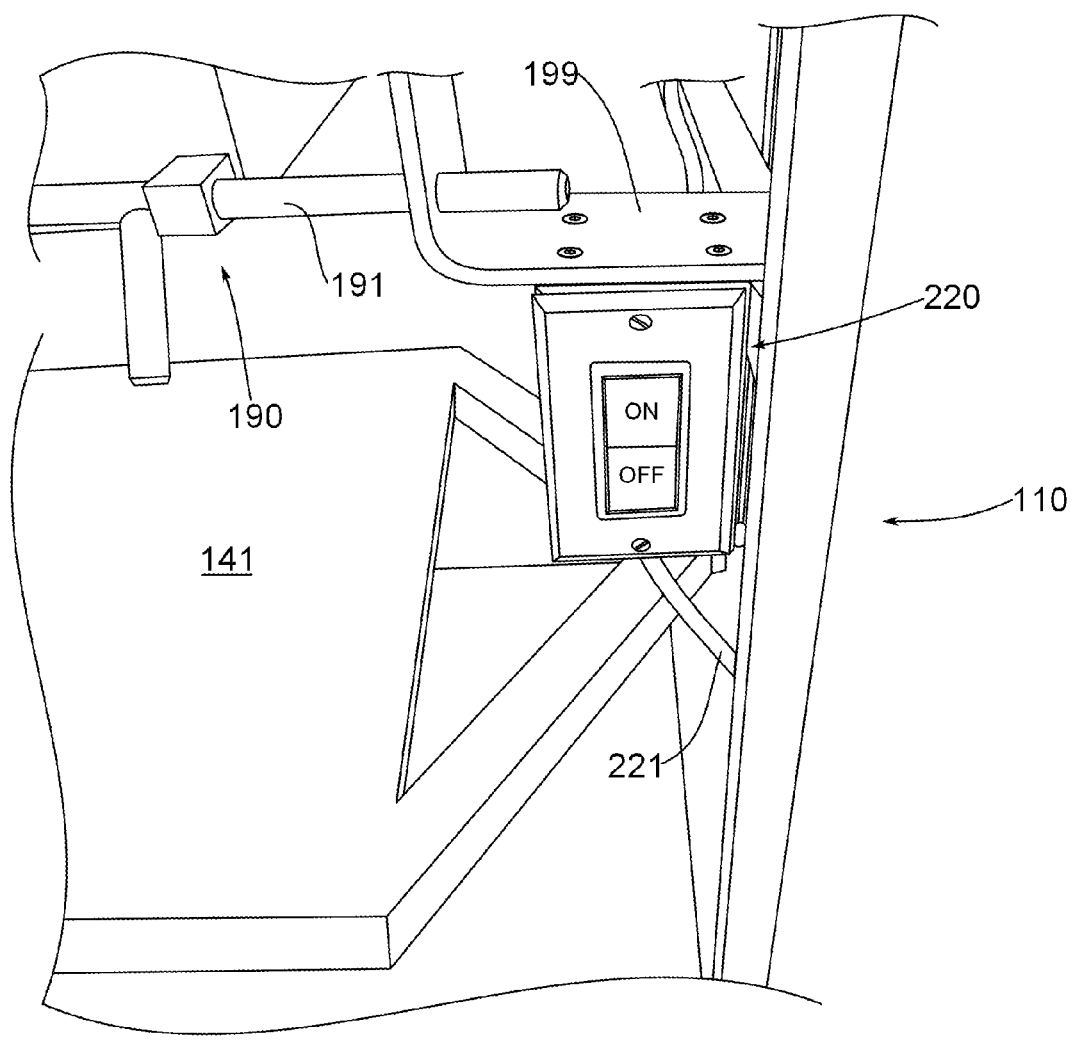
FIG. 5 is a perspective illustration of an electric switch and latch for the inverting candling table of FIG. 4.
Figure 6:
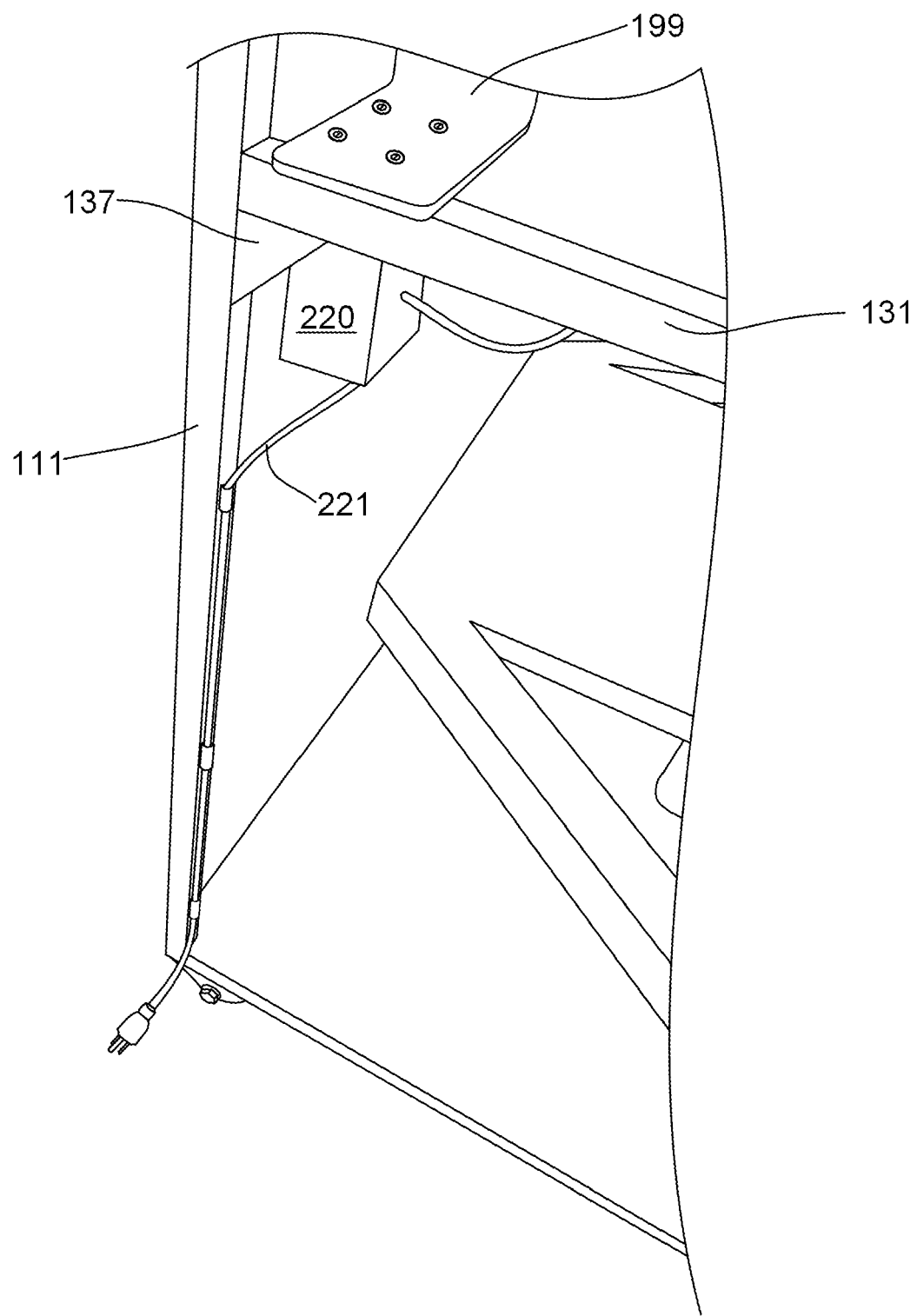
FIG. 6 is an additional perspective illustration of the latch for the inverting candling table of FIG. 4.

FIGS. 5 and 6 are perspective illustrations of an electric switch 220 and latch for the inverting candling table of FIG. 4. The electric switch 220 is conveniently positioned about hip high on the framework 110. The switch has two positions: "ON" and "OFF". When the switch is in the "on" position, power is routed through the switch to the electric lamps in the pan 151. Power is provided to the switch 220 by electric cord 221.

Figure 7:
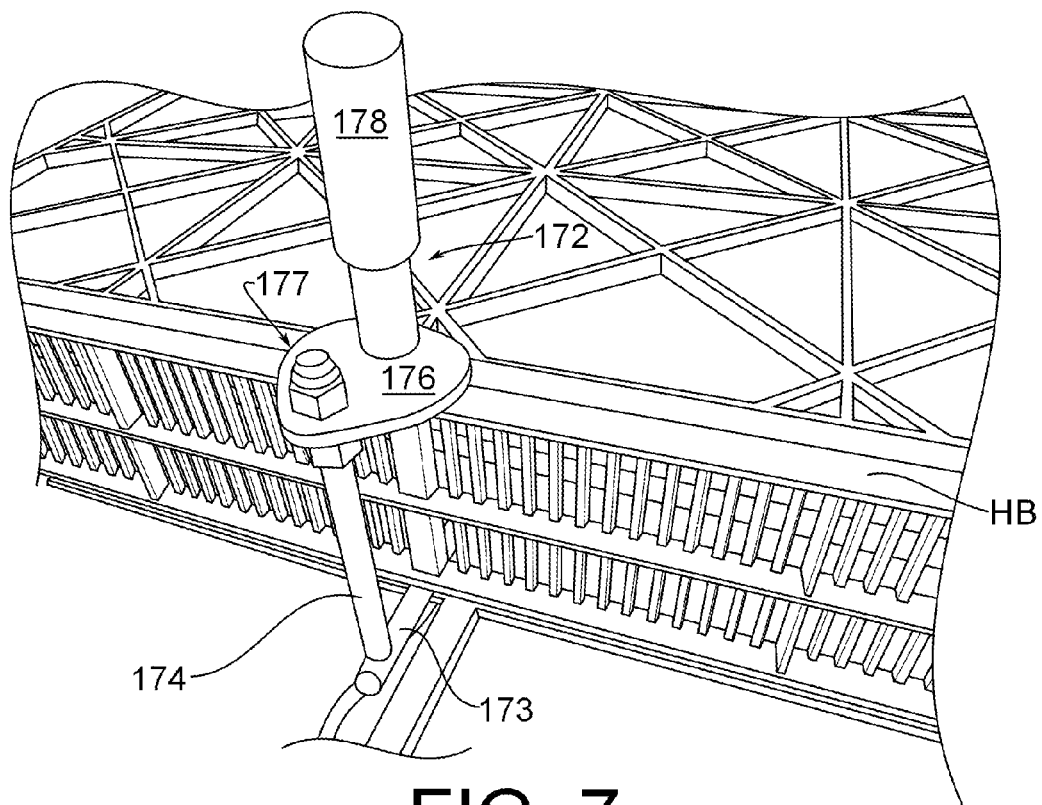
FIG. 7 is a perspective illustration of the inverting candling table portion of the portable egg candling and containment transfer apparatus of FIG. 1, and depicting a hand-operated clamp for securing a hatchery basket to the inverting candling table.

FIG. 7 is a perspective illustration of the inverting candling table portion of the portable egg candling and containment transfer apparatus 100 depicting one of the hand-operated clamps 171, 172 for securing a hatchery basket to the inverting candling table. Each of the hand-operated clamps includes a horizontal shaft 173, a vertical shaft 174 welded thereto and a cam face or clamping face pivotally secured to the upright shaft by a nut and washer arrangement 177. The vertical handle 178 is welded to the clamping face to allow the user to manipulate the clamp to swing the clamping face into engagement with a hatchery basket HB for securing the hatchery basket in place.

Figure 8:
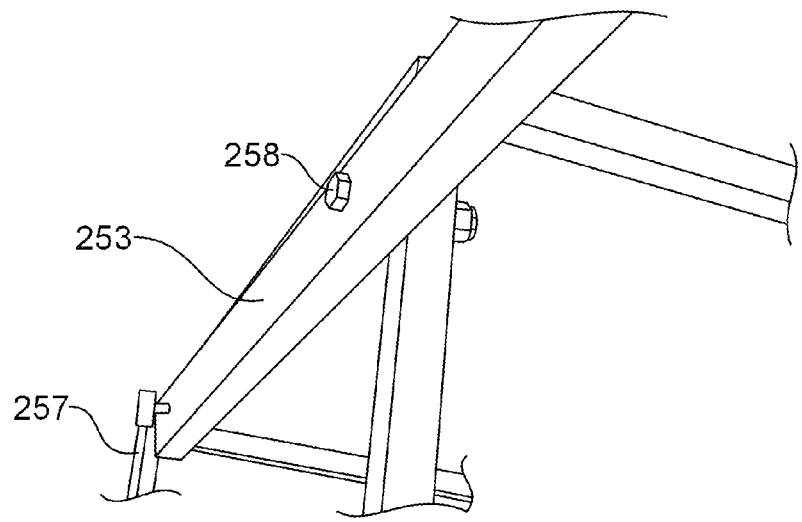
FIG. 8 is a perspective illustration of a portion of a hand-operated raising and lowering mechanism of the portable egg candling and containment transfer apparatus of FIG. 1.

As shown in FIGS. 1 and 8, a raising and lowering mechanism 250 is pivotally secured to the canopy portion of the frame. The raising and lowering mechanism 250 includes an elevator lift handle 251 extending between lever arms 252 and 253. Each of the lever arms is mounted for pivoting motion relative to the upper canopy. The elevator lift handle 251 is secured at the distal ends of the lever arms 252 and 253. At the opposite ends of the lever arms, lifting rods or lifting cables 256 and 257 are connected and extend downward lead to the end of the elevator platform. At the ends of the lift cable or lift rod, the lift cables or lift rods are attached by ball and socket connectors to allow for the parts to rotate relative to one another and provide smooth operation. Additionally, attached to a side of the stanchion 111 is a holding hook 260. The holding hook 260 is rotatably attached to the stanchion 111 and engages with an arm protrusion 261 located on the lever arm 252. When the holding hook 260 is engaged with the protrusion 261, the lever arms 252, 253 are held in stationary place, as seen in FIG. 1.

FIG. 8 is a perspective illustration of a portion of the hand-operated raising and lowering mechanism 250 of the portable egg candling and containment transfer apparatus of FIG. 1, showing the connection of the lifting cables/lifting rods to the lever arms using ball-and-socket connections. These figures also show the pivot axle (here an axle bolt) 258 allowing pivotal motion between the lever arms and the canopy.

Figure 9:
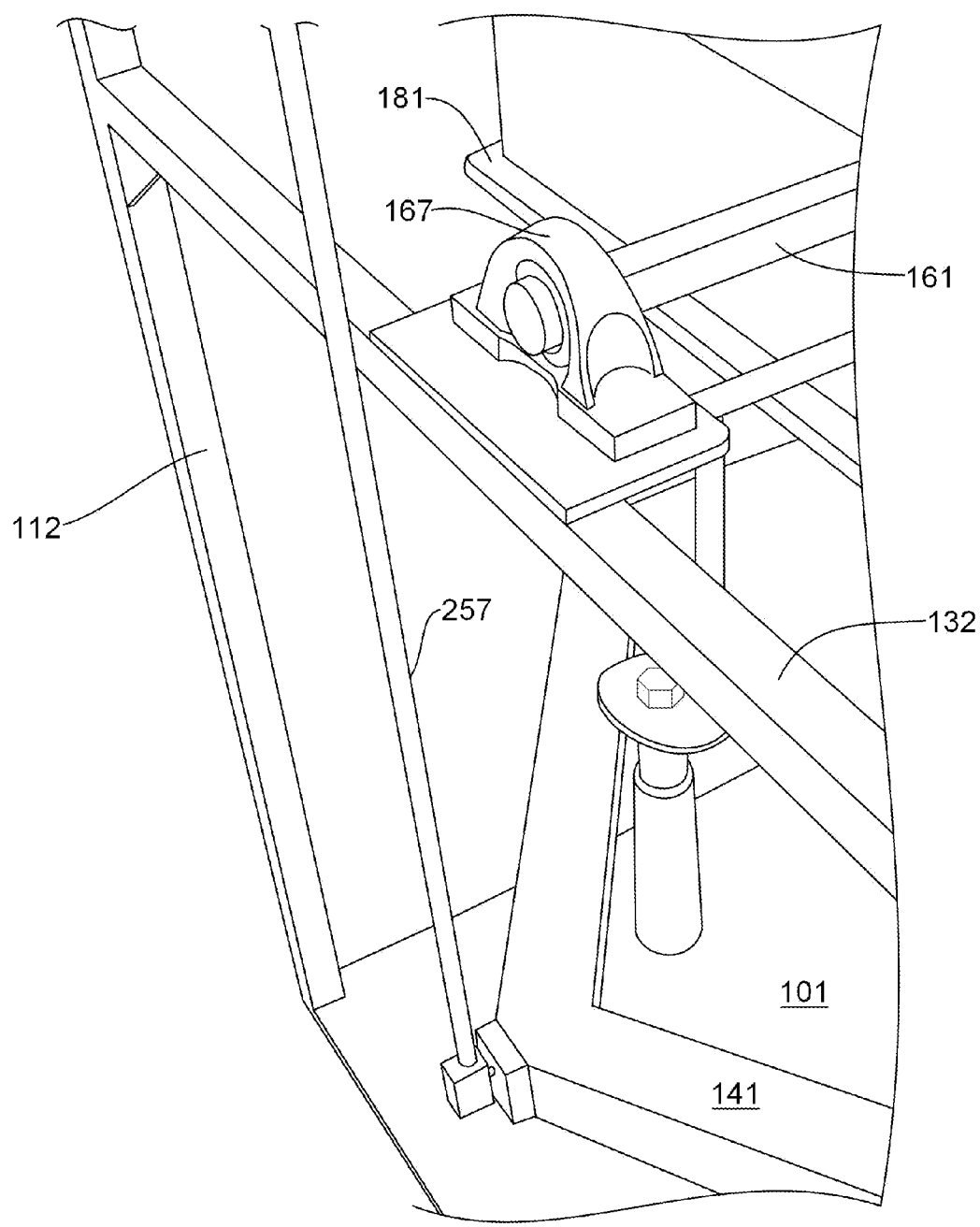
FIG. 9 is an additional perspective illustration of a second portion of the hand-operated raising and lowering mechanism of the portable egg candling and containment transfer apparatus of FIG. 1, and depicting a cable or rod secured to a movable elevator deck and further depicting the attachment of the inverting candling table to the frame of the apparatus.

FIG. 9 is an additional perspective illustration of a lower portion of the hand-operated raising and lowering mechanism 250 of the portable egg candling and containment transfer apparatus of FIG. 1. FIG. 9 depicts the cable or rod secured to the movable elevator deck 141 and further depicts the attachment of the inverting candling table to the frame of the apparatus 100.

Figure 10:
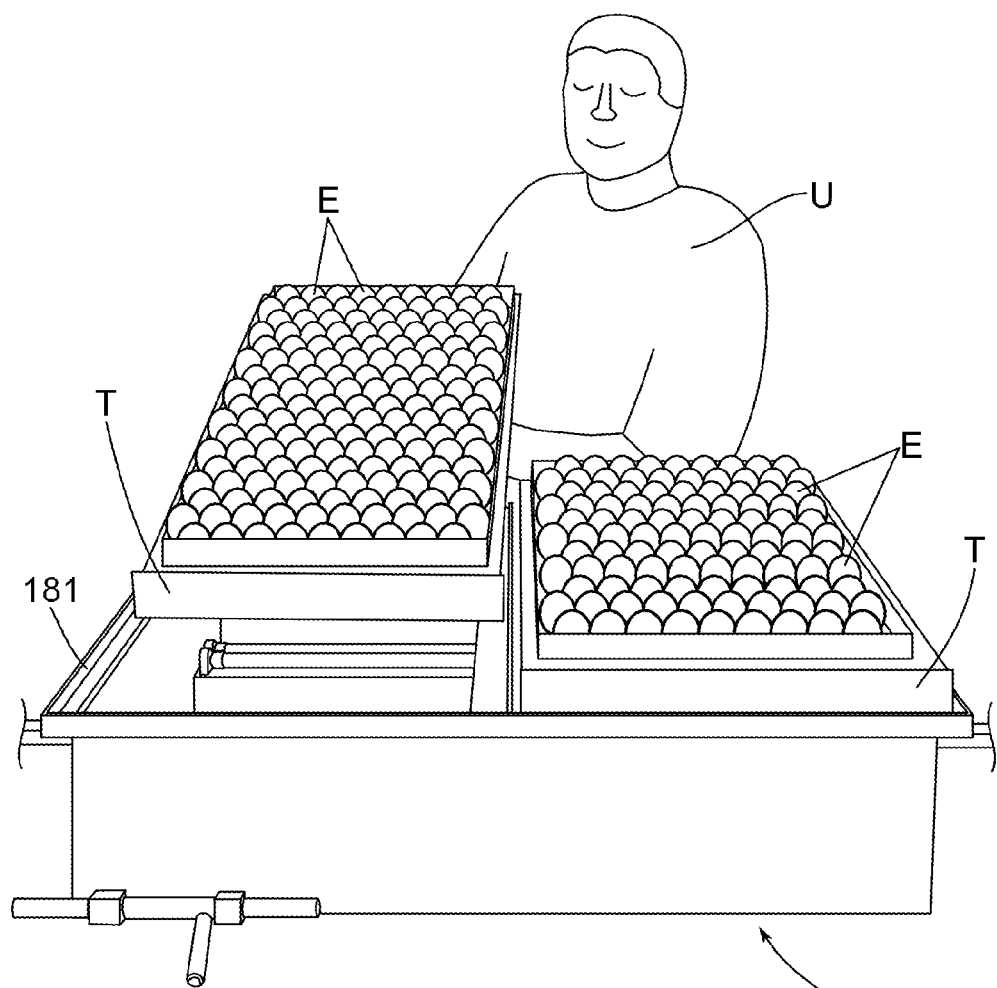
FIG. 10 depicts a first step in using the portable egg candling and containment transfer apparatus of FIG. 1.
Figure 11:
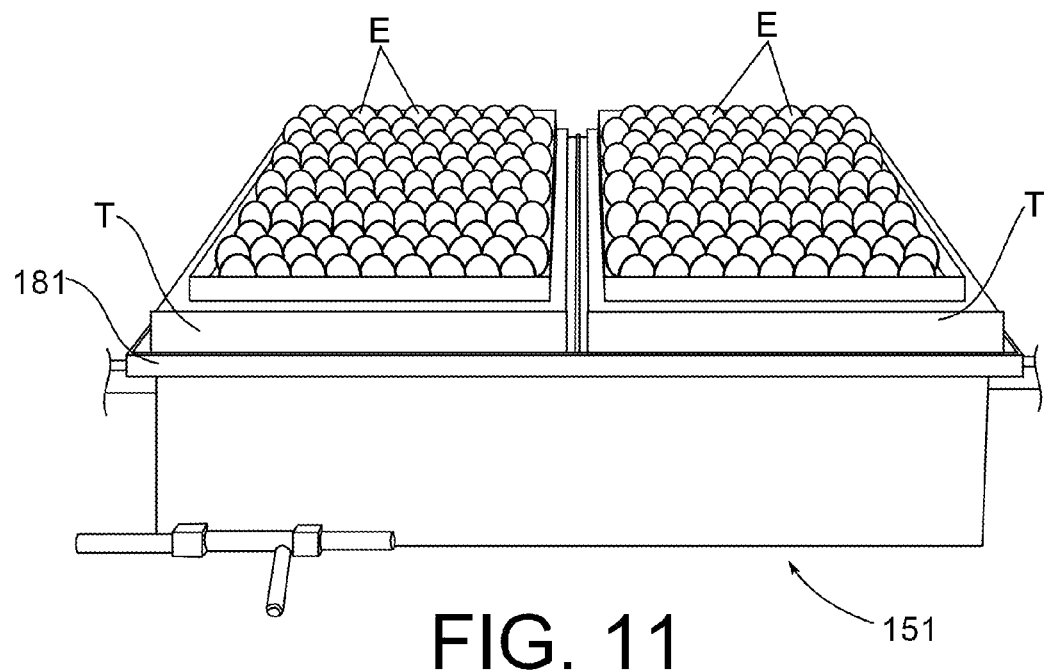
FIG. 11 depicts the portable egg candling and containment transfer apparatus of FIG. 1 after the first step of FIG. 10.

FIG. 10 depicts a first step in using the portable egg candling and containment transfer apparatus 100. Before commencing with the first step, the apparatus 100 can optionally be locked in place by securing the locking casters 102 on the base 101 of the apparatus 100. An operator or user U then loads incubator trays T containing eggs E therein into the pan 151. The trays T are preferably made of a translucent material that is able to transmit light therethrough. Additionally, the trays T can have apertures or openings on their respective bottom faces to allow light to be transmitted therethrough. The trays are securely held in the pan 151 by the ledge 181. FIG. 11 shows the trays T secured in the pan 151 after the user U has placed them therein.

Figure 12:
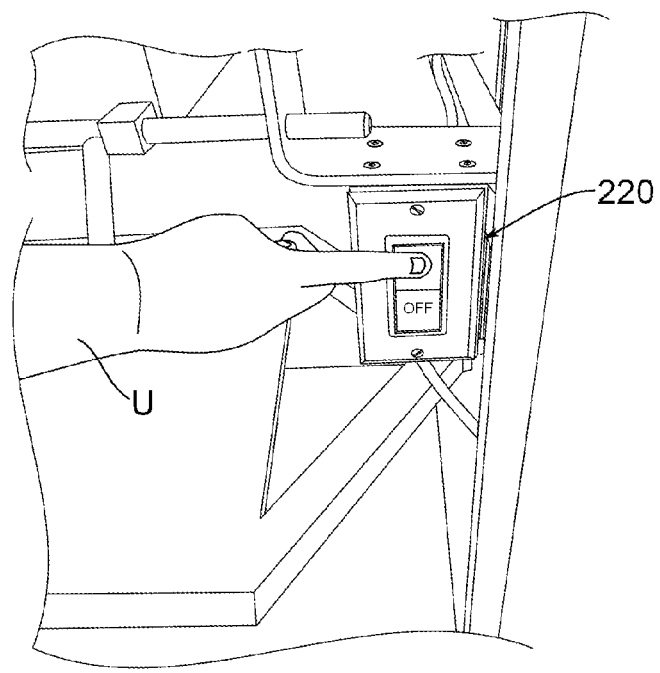
FIG. 12 depicts a second step in using the portable egg candling and containment transfer apparatus of FIG. 1.

FIG. 12 depicts a second step in using the portable egg candling and containment transfer apparatus 100. The user U can toggle the light switch 220 to a powered position, turning on the light fixtures 200, 210 within the pan 151. At this point, the environment surrounding the apparatus 100 is preferably darkened in order to better see the light emanating from the light fixtures 200, 210.

Figure 13:
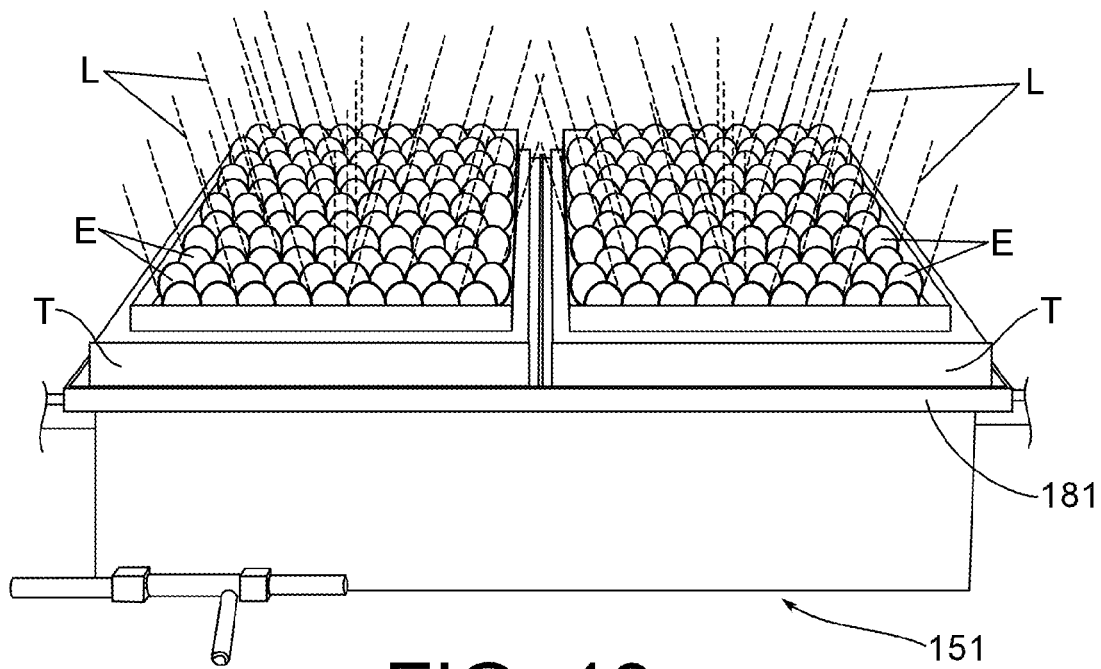
FIG. 13 depicts a third step in using the portable egg candling and containment transfer apparatus of FIG. 1, in which any infertile or defective eggs are removed.

FIG. 13 depicts a third step in using the portable egg candling and containment transfer apparatus 100. Light L emanating from the light fixtures 200, 210 illuminates and candles the eggs E. As the light L is shone through the eggs E, the user U can partially see through the eggs E and defective and/or infertile eggs can be spotted and removed from the trays T by the user U.

Figure 14:
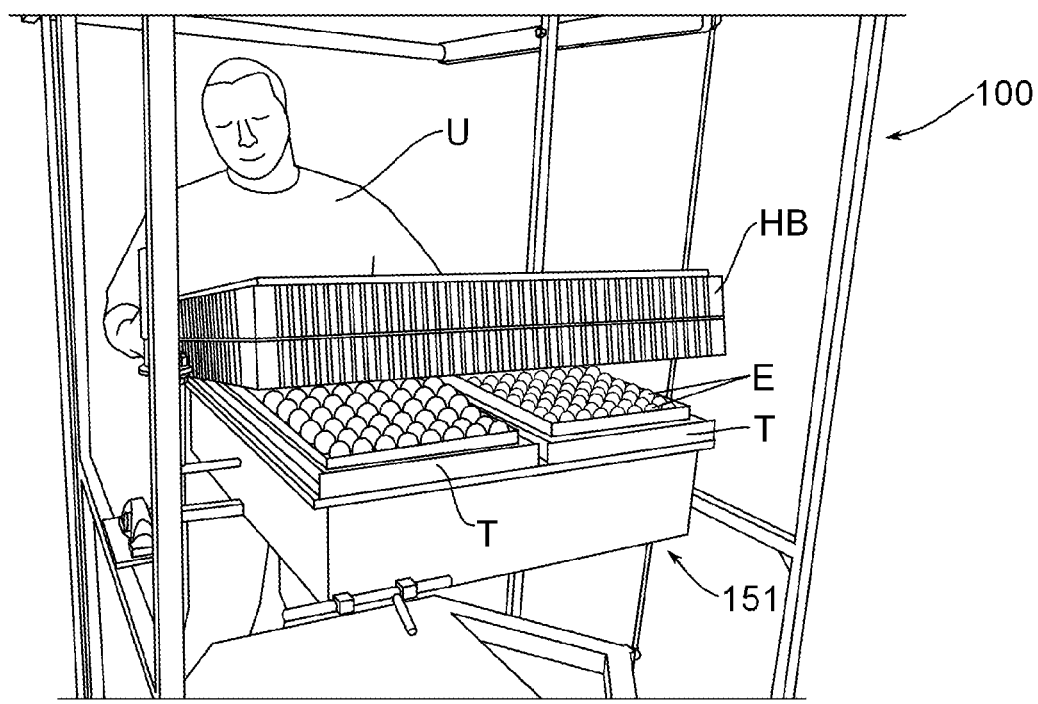
FIG. 14 depicts a fourth step in using the portable egg candling and containment transfer apparatus of FIG. 1, in which a hatchery basket is secured over the incubator trays.

FIG. 14 depicts a fourth step in using the portable egg candling and containment transfer apparatus 100. After any defective and/or infertile eggs are removed from the trays T in the preceding step, a hatchery basket HB is secured over the incubator trays T by the user U. The hatchery basket HB covers the trays T and partially covers a portion of the pan 151.

Figure 15:
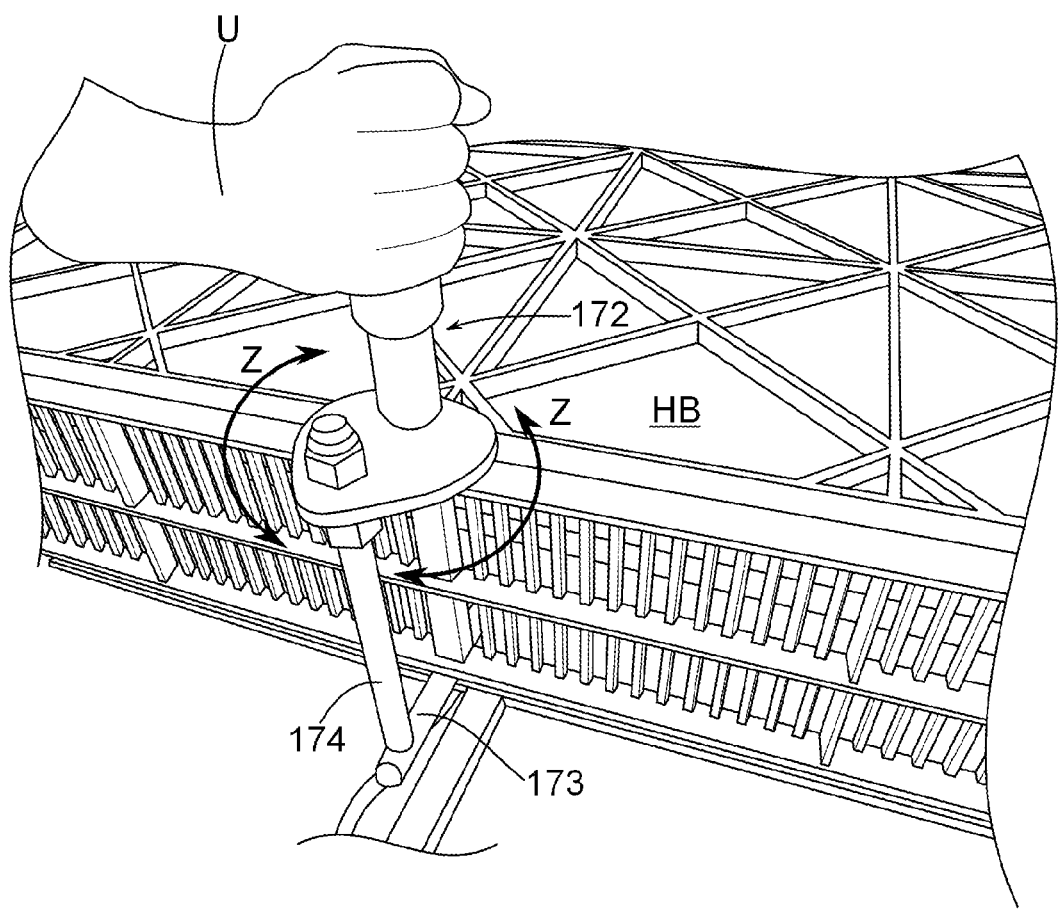
FIG. 15 depicts a fifth step in using the portable egg candling and containment transfer apparatus of FIG. 1, in which the hatchery basket is secured to the apparatus using clamps.

FIG. 15 shows a fifth step in using the portable egg candling and containment transfer apparatus 100. The user U rotates or positions the hand clamps 171, 172 over a portion of the hatchery basket HB and secures the hatchery basket to the apparatus 100. The hand clamps 171, 172 can be rotated in the direction denoted by the arrows Z in order to clamp a portion of the hatchery basket HB to the apparatus 100.

Figure 16:
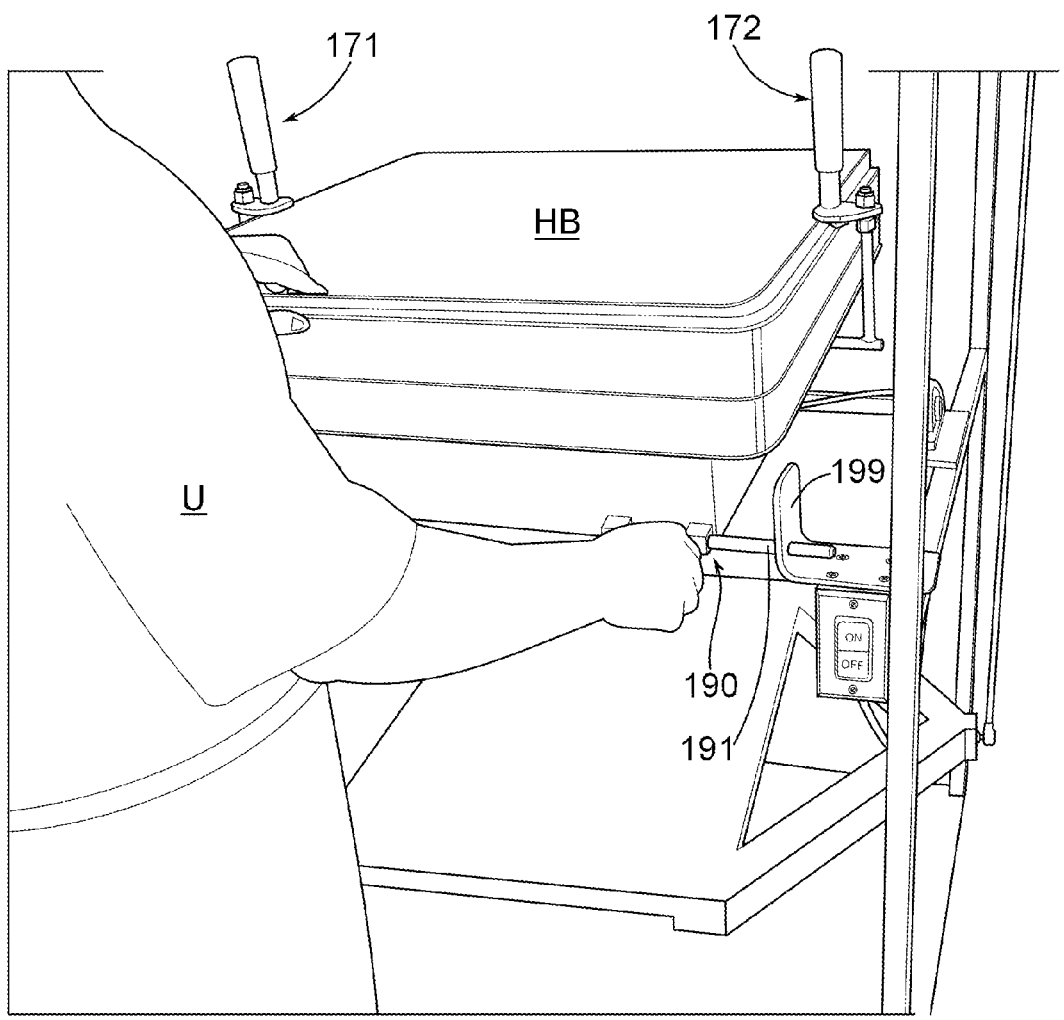
FIG. 16 depicts a sixth step in using the portable egg candling and containment transfer apparatus of FIG. 1, in which an inverting candling table portion of the apparatus is unlatched to ready it to be inverted.
Figure 17:
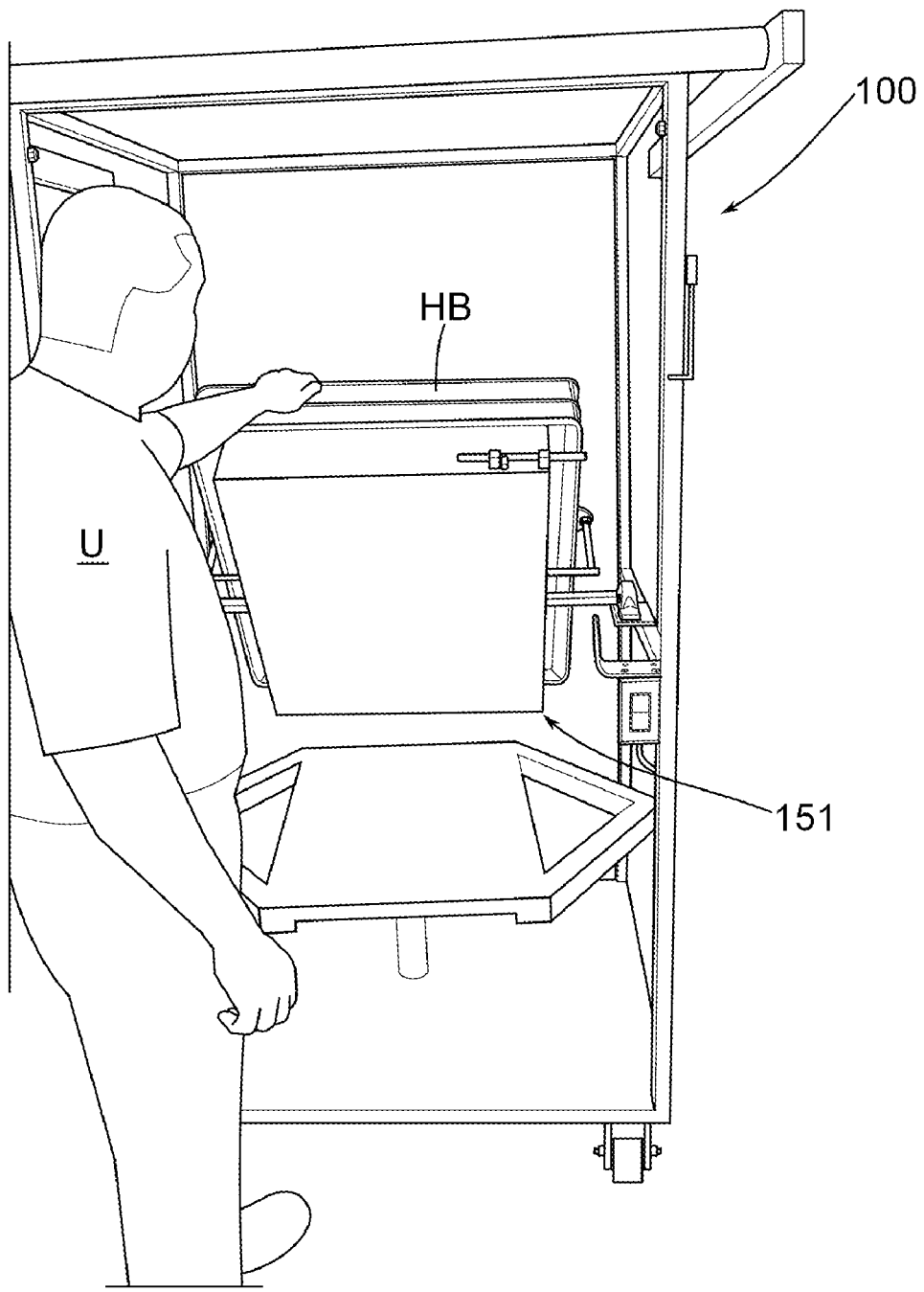
FIG. 17 depicts a seventh step in using the portable egg candling and containment transfer apparatus of FIG. 1, during which the inverting candling table portion of the apparatus is inverted.
Figure 18:
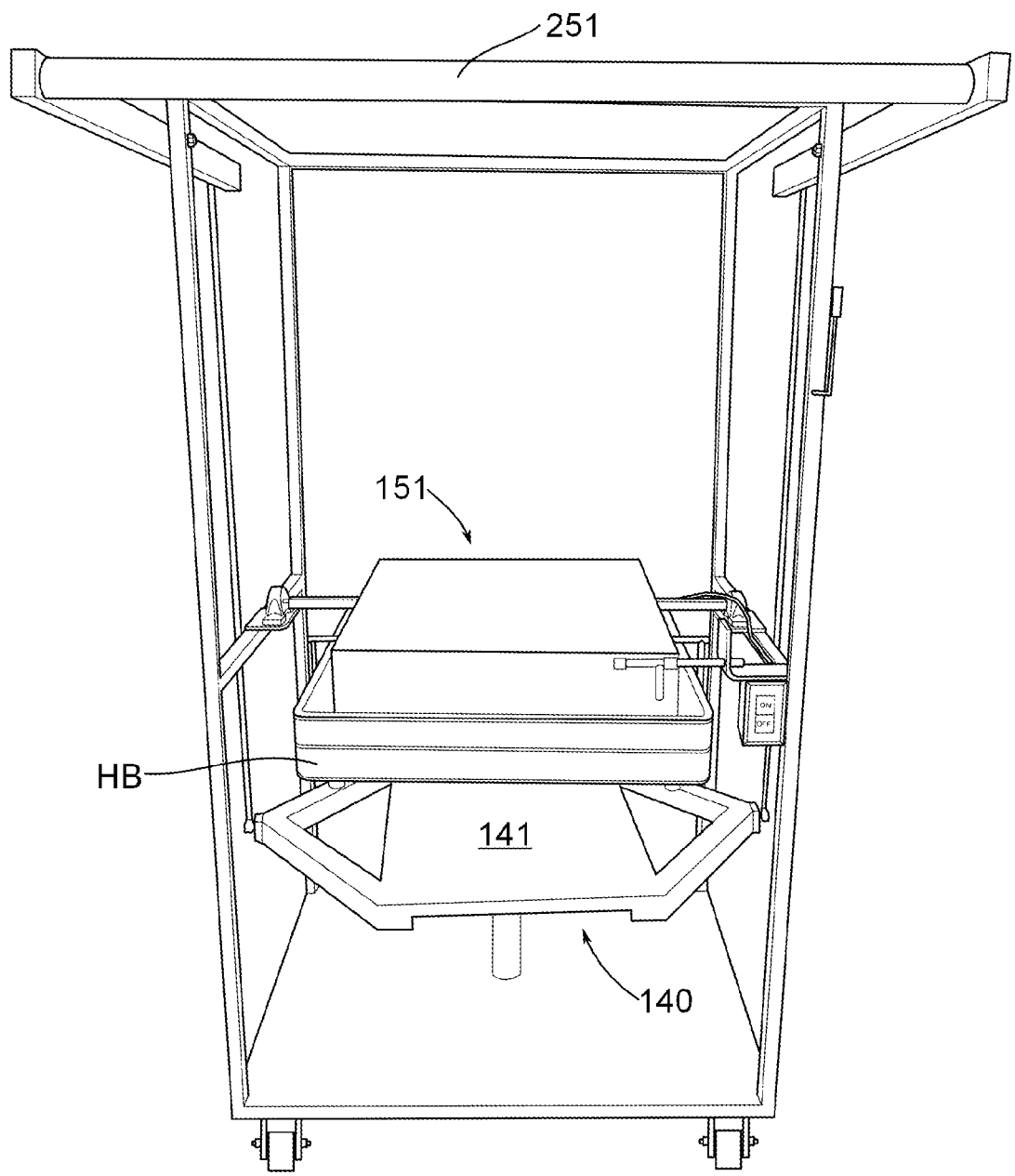
FIG. 18 depicts the portable egg candling and containment transfer apparatus of FIG. 1 after the inversion step (seventh step) of FIG. 17.

FIG. 16 depicts a sixth step in using the portable egg candling and containment transfer apparatus 100. The user U operates the latch 190 to remove the bolt 191 from the latch bolt striker plate 199. This unlocks the inverting candling table 150 and allows it to be inverted, as can be seen in FIG. 17, which represents the seventh step in using the portable candling and containment transfer apparatus 100. The table 150 can be seen fully inverted in FIG. 18.

Figure 19:
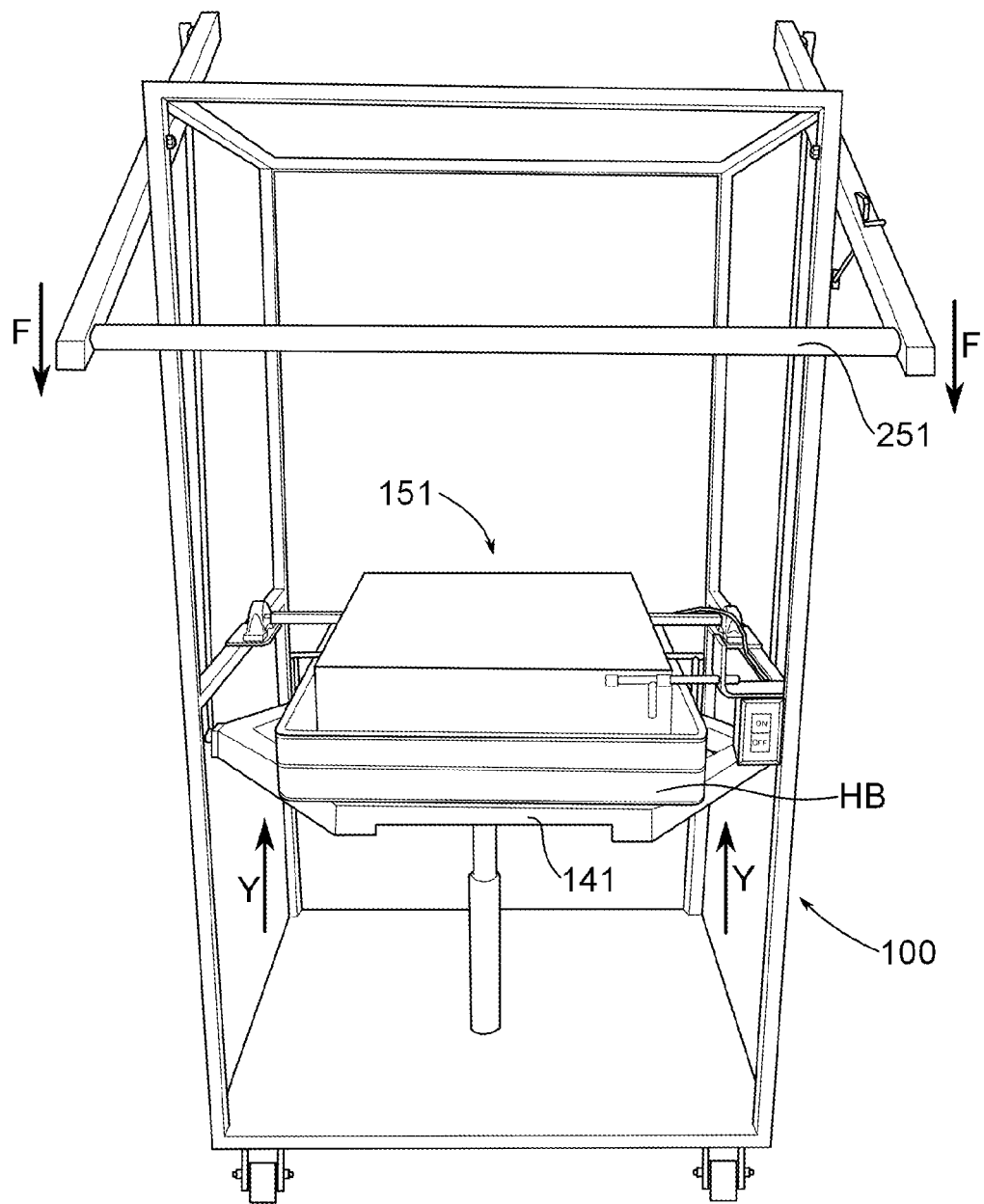
FIG. 19 depicts an eighth step in using the portable egg candling and containment transfer apparatus of FIG. 1, in which an overhead handle is lowered to raise an elevator deck to support the inverted hatchery basket to prepare it to be released from the inverted candling table.

FIG. 19 depicts an eighth step in using the portable egg candling and containment transfer apparatus of FIG. 1. The overhead handle 251 is lowered in the direction denoted by the arrows F to raise an elevator deck 141 upwards in the direction denoted by the arrows Y to support the inverted hatchery basket HB to prepare it to be released from the inverted candling table 150. The holding hook 260 can then be engaged with the arm protrusion 261, which prevents the handle 251 from being raised and the elevator deck 141 from being lowered when the user releases the handle 251. At this point, the clamps 171, 172 can be released from holding the hatchery basket HB. The hatchery basket HB then rests on the elevator deck 141. The hook 260 can then be released from engagement with the protrusion 261, which allows the handle 251 to be raised, thus allowing the elevator deck 141 holding the hatchery basket HB to be lowered.

Figure 20:
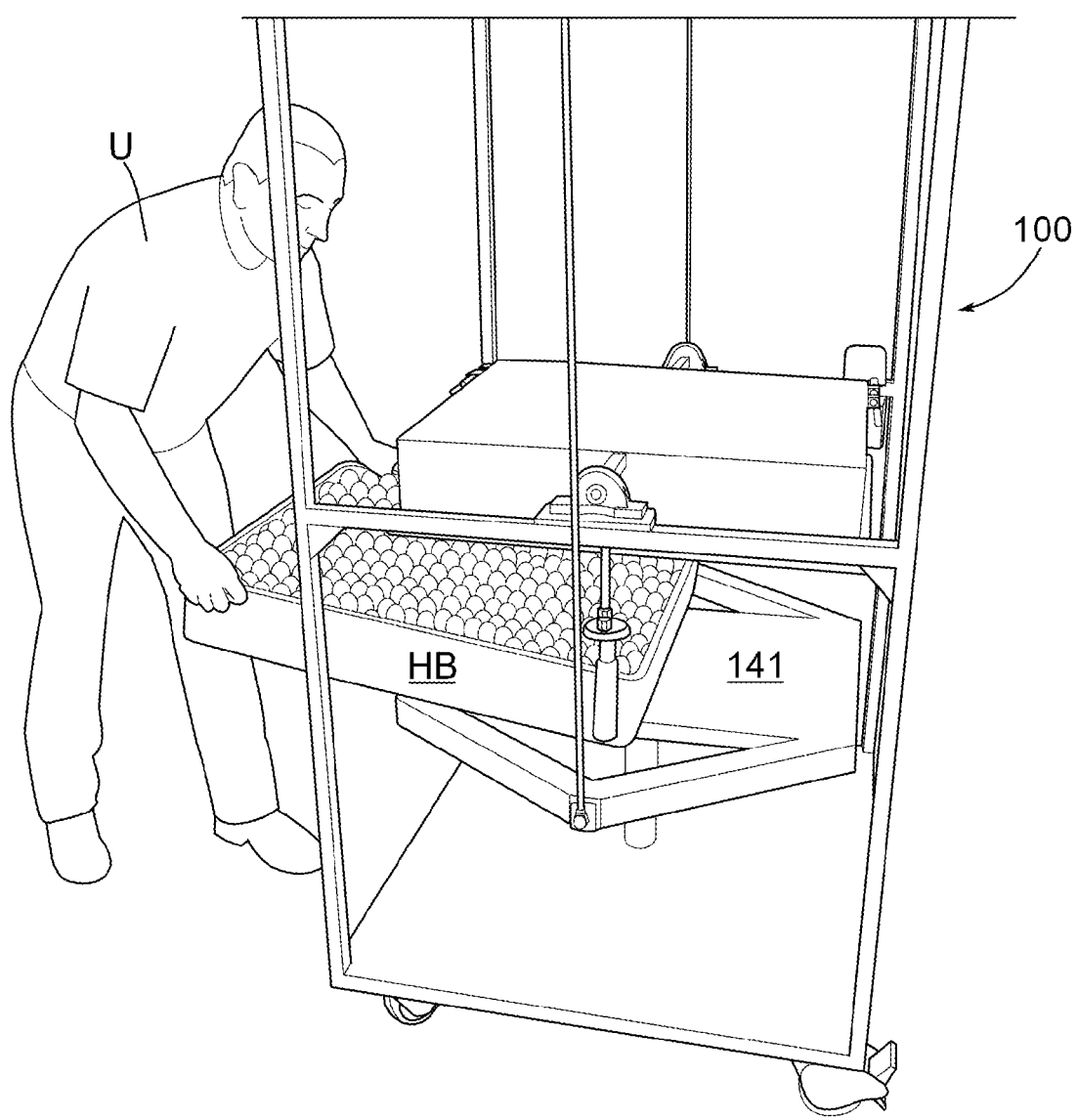
FIG. 20 depicts a ninth step in using the portable egg candling and containment transfer apparatus of FIG. 1, in which the user removes the inverted hatchery basket for stacking and return to an incubator for further incubation and hatching.

FIG. 20 depicts a ninth step in using the portable egg candling and containment transfer apparatus 100. After the elevator deck 141 has been fully lowered, the user U removes the inverted hatchery basket HB for stacking and return to an incubator for further incubation and hatching. The process for using the apparatus 100 can then be repeated over and over to candle, sort, invert, and unload eggs.

While this invention has been described in detail with particular reference to exemplary embodiments and variations thereof, it is to be understood that other variations and modifications can be effected within the scope and spirit of the invention, as described above and as defined in the appended claims.

What is claimed is:

1. A portable egg candling and containment transfer apparatus for use with incubator trays and hatchery baskets, the portable egg candling and containment transfer apparatus comprising:
a movable frame;
a movable elevator deck supported upon the movable frame mounted for translation between an elevated position and a lowered position;
a lever for raising and lowering the movable elevator deck;
an inverting candling table pivotally mounted to the frame and positioned over the movable elevator deck and having a pan with sidewalls and a floor, the pan being adapted for supporting incubator trays positioned thereover, the pan housing at least one electric light fixture with at least one lamp for producing light for candling eggs positioned over the inverting candling table, the inverting candling table pivotally mounted for movement between a first, faceup orientation and a second facedown orientation;
at least one clamp for securing a hatchery basket over the pan; and
at least one latch for securing the inverting candling table in faceup/facedown orientations, wherein the movable elevator deck and the inverting candling table are configured and operable to allow an operator to place eggs in the inverting candling table, to candle the eggs, to invert the eggs to transfer the eggs from an incubator tray to a hatchery basket, to raise the movable elevator deck to allow the eggs and hatchery basket to be released safely from the inverting candling table, and to lower the movable elevator deck to allow the eggs and hatchery basket to be removed.

2. A portable egg candling and containment transfer apparatus as claimed in claim 1 wherein the movable frame includes wheels, with at least two of the wheels being lockable for securing the movable frame in a stable position.

3. A portable egg candling and containment transfer apparatus as claimed in claim 1 wherein the movable frame comprises upright stanchions.

4. A portable egg candling and containment transfer apparatus as claimed in claim 3 wherein the movable frame further comprises cross rails extending between the upright stanchions and wherein the inverting candling table is pivotally mounted to the cross rails.

5. A portable egg candling and containment transfer apparatus as claimed in claim 1 wherein the lever for raising and lowering the movable elevator deck is hand-operated.

6. A portable egg candling and containment transfer apparatus as claimed in claim 1 further comprising a catch for securing the movable elevator deck in the raised position.

7. A portable egg candling and containment transfer apparatus as claimed in claim 1 wherein the pan includes a peripheral ledge for supporting incubator trays and an upstanding lip for positioning the incubator trays over the peripheral ledge and wherein cutouts are formed in the peripheral ledge to provide hand access for grasping edges of the incubator trays.

8. A portable egg candling and containment transfer apparatus as claimed in claim 1 further comprising a hand-operated electric switch for controlling the at least one lamp.

9. A portable egg candling and containment transfer apparatus as claimed in claim 1 wherein the at least one clamp comprises a pair of hand-operated clamps.

10. A portable egg candling and containment transfer apparatus as claimed in claim 1 wherein the lever for raising and lowering the movable elevator deck comprises an overhead handle which can be grasped and pulled downwardly to raise the movable elevator deck.

11. A portable egg candling and containment transfer apparatus for use with incubator trays and hatchery baskets, the portable egg candling and containment transfer apparatus comprising:
a movable frame;
a movable elevator deck supported upon the frame and mounted for translation between an elevated position and a lowered position;
an inverting candling table pivotally mounted to the frame and positioned over the movable elevator deck and having a pan with sidewalls and a floor, the pan being adapted for supporting incubator trays positioned thereover, the pan housing at least one electric light fixture with at least one lamp for producing light for candling eggs positioned over the inverting candling table, the inverting candling table pivotally mounted for movement between a first, faceup orientation and a second facedown orientation, wherein the inverting candling table is operative to invert eggs to transfer the eggs from an incubator tray to a hatchery basket as the inverting candling table is inverted from the faceup orientation to the facedown orientation;
at least one clamp for securing a hatchery basket over the pan;
at least one latch for securing the inverting candling table in faceup/facedown orientations; and
a manually operated handle for raising and lowering the movable elevator deck, wherein the handle can be grasped and pulled downwardly to raise the movable elevator deck.

* * * * *